(12) United States Patent
Schaeppi et al.

(10) Patent No.: US 12,015,611 B2
(45) Date of Patent: *Jun. 18, 2024

(54) SYSTEMS AND METHODS TO DETERMINE CONTENT TO PRESENT BASED ON INTERACTION INFORMATION OF A GIVEN USER

(71) Applicant: Solsten, Inc., Edina, MN (US)

(72) Inventors: Joseph Jack Schaeppi, Maple Grove, MN (US); Lynn Danielle Francoise Bergmann, Berlin (DE); Lloyd William West, Berlin (DE); Jonna Maarit Koivisto, Berlin (DE)

(73) Assignee: Solsten, Inc., Edina, MN (US)

( * ) Notice: Subject to any disclaimer, the term of this patent is extended or adjusted under 35 U.S.C. 154(b) by 287 days.

This patent is subject to a terminal disclaimer.

(21) Appl. No.: 17/528,968

(22) Filed: Nov. 17, 2021

(65) Prior Publication Data
US 2022/0239653 A1    Jul. 28, 2022

Related U.S. Application Data

(63) Continuation of application No. 17/157,712, filed on Jan. 25, 2021, now Pat. No. 11,206,263.

(51) Int. Cl.
*H04L 29/06* (2006.01)
*G16H 10/60* (2018.01)
(Continued)

(52) U.S. Cl.
CPC ............. *H04L 63/10* (2013.01); *G16H 10/60* (2018.01); *H04L 67/306* (2013.01); *H04L 67/535* (2022.05)

(58) Field of Classification Search
CPC ..... H04L 63/10; H04L 67/306; H04L 67/535; G16H 10/60; G16H 20/70; G06Q 30/0201; G06Q 30/0631
(Continued)

(56) References Cited

U.S. PATENT DOCUMENTS

| 8,000,000 B2 | 8/2011 | Greenberg |
| 8,086,491 B1 | 12/2011 | Matz |

(Continued)

FOREIGN PATENT DOCUMENTS

| WO | 0106825 A2 | 2/2001 |
| WO | 2021247465 | 12/2021 |

OTHER PUBLICATIONS

App User Segmentation: Best Practices & Examples; Kadir Soner; https://appsamurai.com/app-user-segmentation-best-practices-examples/; Sep. 22, 2016; [retrieved from the internet on Apr. 21, 2020].

(Continued)

*Primary Examiner* — Tu T Nguyen (74) *Attorney, Agent, or Firm* — Esplin & Associates, PC (57) ABSTRACT

Systems and methods to determine content to present based on interaction information of a given user are disclosed. Exemplary implementations may: store, in electronic storage, psychological profiles; obtain, in an ongoing manner, interaction information of users from the online platforms; determine psychological profiles of the users based on the interaction information for the individual users; update, in an ongoing manner, the determined psychological profiles as the interaction information is ongoingly obtained such that the first psychological profile is ongoingly updated as the first interaction information is ongoingly obtained; and provide, based on the psychological profiles, the individual users with content.

18 Claims, 3 Drawing Sheets

(51) Int. Cl.
  *H04L 9/40* (2022.01)
  *H04L 67/306* (2022.01)
  *H04L 67/50* (2022.01)
(58) Field of Classification Search
  USPC .......................................................... 726/28
  See application file for complete search history.

(56) References Cited

U.S. PATENT DOCUMENTS

| | | |
|---|---|---|
| 8,683,348 B1 | 3/2014 | Blank |
| 9,561,439 B2 | 2/2017 | Oono |
| 10,332,122 B1 | 6/2019 | Engstrom |
| 10,387,173 B1 | 8/2019 | Paulus |
| 10,678,570 B2 | 6/2020 | Zarlengo |
| 10,832,154 B2 | 11/2020 | Kashyap |
| 10,881,964 B1 | 1/2021 | Dills |
| 10,987,592 B1 | 4/2021 | Schaeppi |
| 2004/0097287 A1 | 5/2004 | Postrel |
| 2005/0240444 A1 | 10/2005 | Wooten |
| 2007/0033084 A1 | 2/2007 | Mascarenhas |
| 2007/0233671 A1 | 10/2007 | Oztekin |
| 2008/0045317 A1 | 2/2008 | Seelig |
| 2008/0081701 A1 | 4/2008 | Shuster |
| 2008/0126277 A1 | 5/2008 | Williams |
| 2009/0054123 A1 | 2/2009 | Mityagin |
| 2009/0076845 A1 | 3/2009 | Bellin |
| 2010/0022301 A1 | 1/2010 | Carpenter |
| 2010/0035220 A1 | 2/2010 | Herz |
| 2010/0083318 A1 | 4/2010 | Weare |
| 2010/0179950 A1 | 7/2010 | Willcock |
| 2010/0227302 A1 | 9/2010 | Mcgilvery |
| 2011/0035280 A1 | 2/2011 | Fordyce, III |
| 2012/0015737 A1 | 1/2012 | Craine |
| 2012/0022944 A1 | 1/2012 | Volpi |
| 2012/0036448 A1 | 2/2012 | John |
| 2012/0036449 A1 | 2/2012 | Minnis |
| 2012/0054040 A1 | 3/2012 | Bagherjeiran |
| 2012/0124062 A1 | 5/2012 | Macbeth |
| 2012/0142429 A1 | 6/2012 | Muller |
| 2012/0317064 A1 | 12/2012 | Hagiwara |
| 2013/0041759 A1 | 2/2013 | Mikan |
| 2013/0111509 A1 | 5/2013 | Guo |
| 2013/0304686 A1 | 11/2013 | Antin |
| 2014/0001205 A1 | 1/2014 | Hodges |
| 2014/0017648 A1 | 1/2014 | Williams |
| 2014/0019443 A1 | 1/2014 | Golshan |
| 2014/0094311 A1 | 4/2014 | Kikuchi |
| 2014/0128166 A1 | 5/2014 | Tam |
| 2014/0156681 A1 | 6/2014 | Lee |
| 2014/0179408 A1 | 6/2014 | Ducheneaut |
| 2014/0195303 A1 | 7/2014 | Jarrett |
| 2015/0254995 A1 | 9/2015 | Rosenfeld |
| 2015/0279227 A1 | 10/2015 | Huber |
| 2015/0332603 A1 | 11/2015 | Aravkin |
| 2015/0365449 A1 | 12/2015 | Kurata |
| 2016/0015307 A1 | 1/2016 | Kothuri |
| 2016/0067612 A1 | 3/2016 | Ntoulas |
| 2016/0345060 A1 | 11/2016 | Marci |
| 2017/0036116 A1 | 2/2017 | Cohen |
| 2017/0111461 A1 | 4/2017 | Kelman |
| 2017/0149773 A1 | 5/2017 | Kovacs |
| 2017/0186334 A1 | 6/2017 | Sasidhar |
| 2017/0251070 A1* | 8/2017 | Liu ................... G06Q 30/0255 |
| 2018/0015370 A1 | 1/2018 | Sorek |
| 2018/0101860 A1 | 4/2018 | Fleming |
| 2018/0213058 A1 | 7/2018 | Loeb |
| 2019/0130511 A1 | 5/2019 | Davier |
| 2019/0253431 A1* | 8/2019 | Atanda ................... G06F 21/62 |
| 2020/0051450 A1 | 2/2020 | Yeh |
| 2020/0151278 A1* | 5/2020 | Seida ................. G06F 16/9535 |
| 2020/0206637 A1 | 7/2020 | Robbins |
| 2020/0221181 A1 | 7/2020 | Gupta |
| 2020/0320335 A1 | 10/2020 | Shamun |
| 2020/0351537 A1 | 11/2020 | Browy |
| 2020/0401216 A1 | 12/2020 | Sanger |
| 2021/0043031 A1 | 2/2021 | Keilwert |
| 2021/0146258 A1 | 5/2021 | Pedersen |
| 2021/0202045 A1 | 7/2021 | Neumann |
| 2021/0322887 A1 | 10/2021 | Schaeppi |
| 2021/0379495 A1 | 12/2021 | Schaeppi |
| 2022/0342791 A1 | 10/2022 | Schaeppi |
| 2022/0391932 A1 | 12/2022 | Schaeppi |
| 2022/0401844 A1 | 12/2022 | Schaeppi |
| 2023/0177205 A1 | 6/2023 | Schaeppi |
| 2023/0245175 A1 | 8/2023 | Schaeppi |
| 2024/0062908 A1 | 2/2024 | Schaeppi |

OTHER PUBLICATIONS

PCT International Search Report for Application No. PCT/US2021/035096, mailed Jun. 30, 2021, (6 pages).
Advanced Dungeon Dragons Game Master (Year: 1979).
University of Chicago, Nobel Prize Winner James Heckman, Economics of Personality Traits, J. of Human Resources XLIII p. 972-1059 (Year: 2006).
PCT International Search Report and Written Opinion for Application No. PCT/US2022/051224, dated Mar. 1, 2023 (8 pages).
PCT International Search Report and Written Opinion for Application No. PCT/US2023/011637, dated Mar. 24, 2023 (10 pages).
PCT International Search Report and Written Opinion for Application No. PCT/US2022/025379, dated Aug. 18, 2022 (9 pages).
Advanced Dungeon Dragons Game Master (Year: 1979) 240 pages.
PCT International Search Report and Written Opinion for Application No. PCT/US23/76614, mailed Jan. 22, 2024 ( 9 pages).

* cited by examiner

SYSTEMS AND METHODS TO DETERMINE CONTENT TO PRESENT BASED ON INTERACTION INFORMATION OF A GIVEN USER

FIELD OF THE DISCLOSURE

The present disclosure relates to systems and methods to determine content to present based on interaction information of a given user.

BACKGROUND

Online platforms may be dynamic to tailor their content to individual users. Current techniques of tailoring the content to the individual users may include collecting personal identification information, tracing interactions of individual users, and/or other techniques that may invade user privacy as the user privacy in online settings is becoming more and more important to the users.

SUMMARY

One aspect of the present disclosure relates to a system configured to determine appropriate content to present to users based on how the user interacts with online platforms and/or content provided thereof. The determined content may be based particularly on the interactions of the users and not personal identification information of the users (e.g., username/profile). As such, based on ongoingly obtained interaction information that characterizes the interactions of the users, a psychological profile may be determined. Psychological profiles may characterize a user type and content that suits the user type. Thus, content may be provided to the users based on the determined psychological profile. The determined psychological profile may be ongoingly updated as the user continues to interact with the online platforms. Thus, the content provided to the user via the online platforms may be tailored to individual ones of the users as their interactions continue without personally identifying them to maintain anonymity and user privacy.

One aspect of the present disclosure relates to a system configured to determine content to present based on interaction information of a given user. The system may include one or more hardware processors configured by machine-readable instructions, electronic storage, and/or other components. Instruction components may include computer program components. The instruction components may include one or more of interaction information component, profile tracing component, content providing component, and/or other instruction components.

The electronic storage may be configured to store psychological profiles and/or other information. The psychological profiles may characterize a user type and content that suits the user type.

The interaction information component may be configured to obtain interaction information of users from the online platforms. The interaction information may be obtained in an ongoing manner. The interaction information may characterize content engaged with by individual users, engagement by the individual users with the content and/or the online platforms, an/or other interaction information. By way of non-limiting illustration, first interaction information of a first user may be obtained.

The profile tracing component may be configured to determine psychological profiles of the users based on the interaction information for the individual users and/or other information. The psychological profiles may identify the individual users without personal identification information. By way of non-limiting illustration, a first psychological profile may be determined for the first user based on the first interaction information.

The profile tracing component may be configured to update the determined psychological profiles as the interaction information is ongoingly obtained. The determined psychological profile may be updated in an ongoing manner. By way of non-limiting illustration, the first psychological profile may be ongoingly updated as the first interaction information is ongoingly obtained.

The content providing component may be configured to provide the individual users with content and/or other information. The content may be provided based on the psychological profiles and/or other information. The content provided may facilitate further updating of the determined psychological profile and/or may adapt the online platforms to the individual users. By way of non-limiting illustration, first content may be provided to the first user based on the first psychological profile.

As used herein, the term "obtain" (and derivatives thereof) may include active and/or passive retrieval, determination, derivation, transfer, upload, download, submission, and/or exchange of information, and/or any combination thereof. As used herein, the term "effectuate" (and derivatives thereof) may include active and/or passive causation of any effect, both local and remote. As used herein, the term "determine" (and derivatives thereof) may include measure, calculate, compute, estimate, approximate, generate, and/or otherwise derive, and/or any combination thereof.

These and other features, and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of 'a', 'an', and 'the' include plural referents unless the context clearly dictates otherwise.

DETAILED DESCRIPTION

Figure 1:
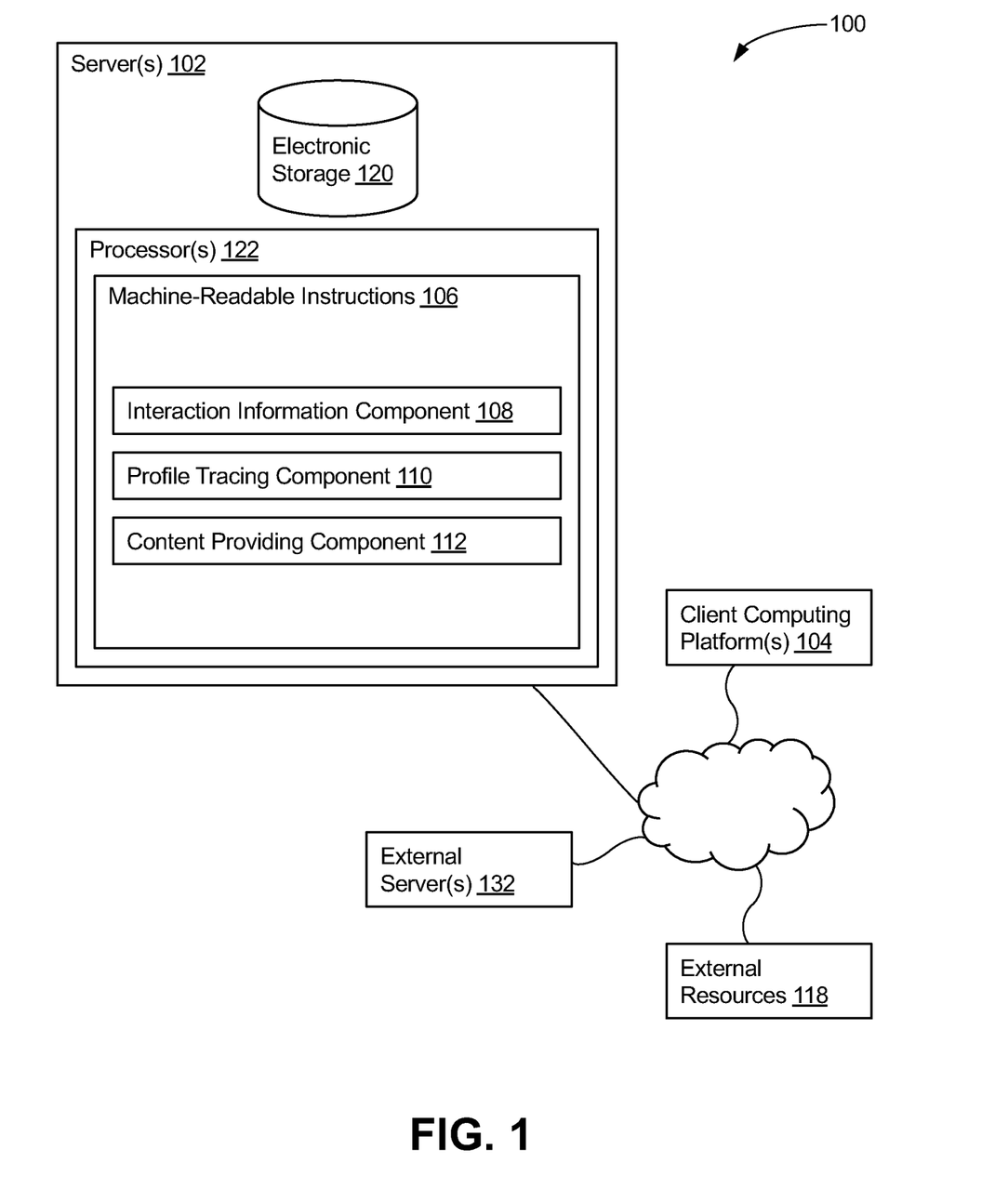
FIG. 1 illustrates a system configured to determine content to present based on interaction information of a given user, in accordance with one or more implementations.

FIG. 1 illustrates a system 100 configured to determine content to present based on interaction information of a given user, in accordance with one or more implementations. In some implementations, system 100 may include one or more servers 102. Server(s) 102 may be configured to communicate with one or more client computing platforms 104 according to a client/server architecture and/or other architectures. Client computing platform(s) 104 may be configured to communicate with other client computing platforms via server(s) 102 and/or according to a peer-to-peer architecture and/or other architectures. Users may access system 100 via client computing platform(s) 104.

In some implementations, external server(s) 132 may be configured to provide and/or host one or more online platforms. External server(s) 132 may refer to an individual (video) game providers, a gaming console, game companies, website developers, user experience companies, and/or a combination thereof. As used herein, "online platform" or variations thereof may include a digital experience. A digital experience may include one or more of a game (e.g., online via web browser, via desktop application, via mobile application, via game console, etc.), a website (e.g., retailers), a mobile application, a desktop application, a social network platform, a service provider (e.g., E-mail provider), and/or other digital experiences. Such digital experiences may collect similar information related to its users and provide some of the same interactions or similar interactions between individual users, between the individual users and virtual content, and/or other interactions. Virtual content (or pieces thereof) may include one or more of game content, social media content, publicity content, and/or other virtual content. The game content may include one or more of a player-controlled character, a non-player-controlled character, a task, a quest, an assignment, a mission, a level, a chapter, a mini-game, a virtual item, a virtual resource (e.g., weapon, tool), an in-game power, an in-game skill, an in-game technology, and/or other pieces of game content. By way of non-limiting example, virtual items may include one or more of clothing, pets, transportation units (e.g., aircrafts, motor vehicles, watercrafts, etc.), units, buildings, and/or other virtual items. The social media content and the publicity content may include one or more of an image, a video, a description, a financial component (e.g., for purchasing, selling, trading, donating, etc.), and/or other content. The online platforms may be accessed by the users via client computing platform(s) 104.

Server(s) 102 may be configured by machine-readable instructions 106. Machine-readable instructions 106 may include one or more instruction components. The instruction components may include computer program components. The instruction components may include one or more of interaction information component 108, profile tracing component 110, content providing component 112, and/or other instruction components.

Electronic storage 120 may be configured to store psychological profiles and/or other information. The psychological profiles may characterize a user type and content that suits the user type. A user type may be defined by multiple psychological parameter values that characterize how a user interacts with the online platforms, why the user interacts with particular online platforms, when the user interacts with the particular online platforms, and/or other user type information. The content that is characterized by the psychological profiles may suit the user type based on the multiple psychological parameter values and/or other information. The content suitable for the user type may entertain, interest, inspire, encourage, and/or otherwise may be appropriate for the user type.

The psychological parameter values may define, by way of non-limiting example, achievement motivation, motivation, personality inventory, cultural values, competitiveness, positive and negative affect before, during, and/or after engagement with the online game (i.e., emotions), communication style, personal values, daily routines/activities, life/gaming pain points, life/gaming hopes and aspirations, wellbeing, user experience, gaming/experience using time, subscription behavior, affinity information, personality, emotional style, goal orientation, goal commitment, ego and task orientation, relatedness, sense of community, social influence, social identity, group identification, we-identity, quality of life, satisfaction with life, work-related quality of life, mindfulness, happiness, emotional intelligence, self-awareness/internal awareness, external awareness, connectedness to nature, social connectedness, social bonding, perceived stress, depression, anxiety, decision-making style, thinking style, critical thinking, cognitive approach to learning, learning style, attributional style, internality-externality, stability-instability, global-specific, creativity, curiosity, playfulness, exploration, mental strength, grit, flourishing, gratitude, inspiration, spirituality, hedonism, materialism/material values, perceptions, sentiments, and/or other psychological parameters.

Achievement motivation may include compensatory effort, competitiveness, confidence in success, dominance, eagerness to learn, engagement, fearlessness, flexibility, flow, goal setting, independence, internality, persistence, preference in difficult tasks, pride in productivity, self-control, status orientation, ambition, self-assurance, and/or other psychological parameters. Motivation may include mastery, purpose, autonomy, and/or other psychological parameters.

Personality inventory may include neuroticism, openness, conscientiousness, extraversion, and agreeableness and/or other psychological parameters. Neuroticism may include anxiety, impulsiveness, vulnerability, and/or other psychological parameters. Openness may include fantasy, feelings/empathy, action, and/or other psychological parameters. Conscientiousness may include achievement striving, competence, self-discipline, and/or other psychological parameters. Extraversion may include warmth assertiveness, activity, and/or other psychological parameters. Agreeableness may include trust, altruism, modesty, and/or other psychological parameters.

Cultural values may include individualism, indulgence, long term orientation, masculinity, power distance, uncertainty avoidance, and/or other psychological parameters. Competitiveness may include avoidant, collaborative, competitive affectivity, dependent, dominant, general competitiveness, independent, personal enhancement, and/or other psychological parameters.

Positive and negative affect before, during, and/or after engaging in the online game may include hostility, joviality, negative emotions, positive emotions, sadness, self-assurance, and/or other psychological parameters. Communication style may include feeler, intuitor, sensor, thinker, and/or other psychological parameters.

Wellbeing may include social wellbeing, psychological wellbeing, physical wellbeing, physical activity, sleep, bounded reciprocity, resilience grit, and/or other psychological parameters.

Personality may include anger, hostility, depression, self-consciousness, excitement-seeking, positive emotions, gregariousness, ideas, values, aesthetics, tender-mindedness, straightforwardness, compliance, deliberation, order, dutifulness, and/or other psychological parameters.

Emotional style may include resilience, outlook, social intuition, self-awareness, sensitivity to context, attention, and/or other psychological parameters.

Goal orientation may include mastery approach/learning goal orientation, performance approach/performance goal orientation, performance avoid/avoidance goal orientation, and/or other psychological parameters.

Work-related quality of life may include structure, boundaries, focus, efficiency, information provision, communication, psychological support, stress at/from work, psychological safety, connectedness with team, motivation to work, adaptability, job/career satisfaction, control at work, homework interface, general wellbeing, working conditions, and/or other psychological parameters.

Mindfulness may include observing, describing, acting with awareness, non-judgment, non-reactivity, and/or other psychological parameters.

Emotional intelligence may include emotion perception, emotion expression, emotion management, emotion regulation, impulse control, relationships, stress management, and/or other psychological parameters.

Social connectedness may include social connectedness, loneliness, membership self-esteem, private self-esteem, public self-esteem identity self-esteem, interdependent self, independent self, social avoidance, social distress, and/or other psychological parameters.

Decision-making style may include respected, confident, spontaneous, dependent, vigilant, avoidant, brooding, intuitive, anxious, and/or other psychological parameters.

Thinking style may include intuitive, experiential, analytical, rational, and/or other psychological parameters.

Cognitive approaches to learning may include avoidant, participative, competitive, collaborative, dependent, independent, and/or other psychological parameters.

Learning style may include visual (spatial), aural (auditory-musical), verbal (linguistic), physical (kinesthetic), logical (mathematical), social (interpersonal), solitary (intrapersonal), and/or other psychological parameters.

Mental strength may include tenacity, confidence, optimism, adaptability, self-awareness, reliability, responsibility, well-being, and/or other psychological parameters.

Flourishing may include positive emotion, engagement, relationships, meaning, accomplishment, health, loneliness, and/or other psychological parameters.

The psychological parameter values of the psychological parameters may be a number score on a predetermined range unique to each psychological parameter, a letter score, and/or other type of value than may characterize intensity of the psychological parameter that the psychological parameter value defines and thus a particular user as whole. The intensity may represent significance of a given psychological parameter of the particular user.

Interaction information component 108 may be configured to obtain interaction information of users from the online platforms and/or other information. The interaction information may be obtained in an ongoing manner. The term "ongoing manner" as used herein may refer to performing an action (e.g., obtaining) continuously or periodically (e.g., every 30 seconds, every minute, every hour, etc.) until receipt of an indication to terminate. The indication to terminate may include exiting the online platforms, exiting a web browser opened to the online platforms, powering off client computing platform 104, selection of a virtual button, and/or other indications of termination. The interaction information may characterize content engaged with by individual users, engagement by the individual users with the content, and/or other interaction information. The content engaged with by the individual users may be related to the online platforms that provide the content. That is, for example, the content provided by an online gaming platform may relate to online games (e.g., virtual goods, virtual mini-games, etc.). In some implementations, the content engaged with by the individual users may not be related to the online platforms that provide the content.

The engagement by the individual users may define behavior patterns of the individual users with or based on the content. The behavior patterns of the individual users may include individual actions, sets of actions, ordered sets of actions, time spent by the individual users engaging with the content and/or the online platforms, spending patterns of the users, completed tasks by the individual users, uncompletion tasks by the individual users, failure of tasks by the individual users, and/or other behavior patterns. In some implementations, the behavior patterns may include multiple of the individual actions, the sets of actions, and the ordered set of actions. The actions may include one or more of a purchase based on the content, a sale, a trade, a donation, a user selection of the content, gameplay (e.g., mini-game, battle, competition, etc.) based on the content, communication of the individual users with other particular users, completion of tasks by the users, frequent interaction with the content, formation of alliances by the users, and/or other actions. The spending patterns may indicate an amount of currency (e.g., real-world money, virtual money, points, etc.) spend, an amount of currency earned, an amount of currency donated, and/or other indications. By way of non-limiting illustration, first interaction information of a first user may be obtained.

Profile tracing component 110 may be configured to determine psychological profiles of the users based on the interaction information for the individual users and/or other information. The psychological profiles may identify the individual users without personal identification information. The personal identification information may include a name, a gender, an age, a username, an email address, a phone number, and/or other personal identification information. The username may be a requirement by individual online platforms and may identify the user on the online platforms that the username is recorded. In some implementations, the individual users may be identified by multiple of the psychological profiles. By way of non-limiting illustration, a first psychological profile may be determined for the first user based on the first interaction information. A purchase based on the content by the first user, for example, may reveal that the first user is impulsive (i.e., a psychological parameter value).

Profile tracing component 110 may be configured to update the determined psychological profiles as the interaction information is ongoingly obtained. The determined psychological profile may be updated in an ongoing manner. The psychological profiles may be updated based on the interaction information ongoingly obtained. Updating the psychological profiles may include determining one or more of the psychological parameter values and the intensity of the one or more psychological parameter values. In some implementations, based on the ongoing updating, one of the psychological profiles may be determined to more closely identify the users subsequent to multiple psychological profiles being determined to identify the users. By way of non-limiting illustration, the first psychological profile may be ongoingly updated as the first interaction information is ongoingly obtained. The first psychological profile may be updated to include a psychological parameter value for impulsiveness psychological parameter. In some implementations, updating the determined psychological profiles may include updating which content is suitable for the user type. Updating which content is suitable may include removing content, adding content, adjusting existing characterized content, and/or other updates.

In some implementations, a psychological profile may be determined and/or the content may be provided without assigning a static user identifier to the individual users. A static user identifier may be a fixed and/or unique identifier (e.g., a number, an alphanumeric identifier) that uniquely distinguishes the individual users from other ones of the users. In some implementations, the psychological profiles determined and ongoingly updated may be identifiers for the individual users. That is, as the psychological profile that was determined ongoingly updates as the interaction information for the individual users is ongoingly obtained from the engagement of the users with the online platforms, the psychological profile that develops is what identifies the individual users as opposed to the user type.

Content providing component 112 may be configured to provide the individual users with content and/or other information. The content may be provided based on the determined psychological profiles and/or other information. The content provided may facilitate further updating of the determined psychological profile and/or may adapt the online platforms to the individual users. In some implementations, the content provided may be for the same online platform the user is presently engaging with or for other online platforms. Providing the content to the individual users may include effectuating presentation of the content via the online platforms or transmitting presentation information, that effectuates the presentation of the content, to the online platforms. By way of non-limiting illustration, first content may be provided to the first user based on the first psychological profile. The first content may be provided to the first user via the online platforms such as a first online platform.

By way of non-limiting example, the content may include one or more of a character, a game, a game asset, a recommendation, a suggestion, a promotion, and/or other content. The character may refer to an object (or group of objects) present in a virtual space that corresponds to an individual user (e.g., an avatar) and/or are controlled by the user. In some implementations, the character may not correspond to an individual user but rather provide information (e.g., the recommendation, the suggestion) to the user. The game asset may include a virtual item, a virtual resource (e.g., weapon, tool), of in-game powers, in-game skills, in-game technologies, and/or other game assets. The recommendation may include a particular selection and/or action that the user is advised to select and/or do. The suggestion may include particular ideas, plans, and/or strategies for the user to consider executing, following, and/or is determined they will enjoy. The promotion may include discount codes, coupons, bonuses, and/or other promotions of the virtual items, products, and/or services that the user may utilize. By way of non-limiting example, products and/or services may relate to beauty (e.g., skincare, makeup), home improvement, decoration, clothing, accessories, technology, kitchen, and/or other categories.

The virtual space may provide an online game and comprise a simulated space that is accessible by users via clients (e.g., client computing platform(s) 104) that present the views of the virtual space to a user. The simulated space may have a topography, express ongoing real-time interaction by one or more users, and/or include one or more objects positioned within the topography that are capable of locomotion within the topography. In some instances, the topography may be a 2-dimensional topography. In other instances, the topography may be a 3-dimensional topography. The topography may include dimensions of the space, and/or surface features of a surface or objects that are "native" to the space. In some instances, the topography may describe a surface (e.g., a ground surface) that runs through at least a substantial section of the space. In some instances, the topography may describe a volume with one or more bodies positioned therein (e.g., a simulation of gravity-deprived space with one or more celestial bodies positioned therein). The instance executed by the computer components may be synchronous, asynchronous, and/or semi-synchronous.

The above description of the manner in which views of the virtual space are provided is not intended to be limiting. The virtual space may be expressed in a more limited, or richer, manner. For example, views determined for the virtual space may be selected from a limited set of graphics depicting an event in a given place within the virtual space. The views may include additional content (e.g., text, audio, pre-stored video content, and/or other content) that describes particulars of the current state of the place, beyond the relatively generic graphics. For example, a view may include a generic battle graphic with a textual description of the opponents to be confronted. Other expressions of individual places within the virtual space are contemplated.

Individual ones of the content may be associated with an engagement level. The engagement level may refer to how appealing the content is so that the user may select or otherwise interact with the content. The engagement level may be a numerical value, a numerical value within a predetermined range (e.g. 1-10), a category (e.g., low, medium, high), and/or other units of measurement. The engagement level may vary based on the psychological profiles and/or other information.

A response or interaction with the content by the users may indicate, reveal, or update one or more of the psychological parameter values and thus the determined psychological profile may be further updated. For example, the first user may frequently follow recommendations provided. Such response may indicate achievement striving and efficiency and thus increase or add psychological parameter values for such. In some implementations, the content provided to the individual users may alter a narrative of the individual online platforms. The narrative may refer to a journey, path, or story of a given online platform (e.g., online game) that the individual users may be following. Based on the determined psychological profile and updates thereof, occurrence of events along the narrative, for example, discovery of a treasure in a virtual game, may be eliminated, inserted, or otherwise adjusted. For example, the discovery of the treasure may occur later in the narrative than previously intended.

In some implementations, the adaptations to online platforms may elicit an intended response. The intended response may be determined by the online platform or administrators thereof. The intended response may include individual ones of the actions or discrete set of the actions by the users. For example, the intended response may be for the users to progress in a game level. In some implementations, the adaptations may tailor the online platforms and its content to the users' liking and/or desires. That is, content that the users may enjoy may be provided. Adaptations may include one or more of providing the recommendation, providing the suggestion, adjusting a difficulty setting, providing availability to a piece of the game content, omitting of one or more pieces of the game content, providing or adjusting means of communication, providing a communication (e.g., textual message, audio message, video message), providing or adjusting an offer to sell one or more the virtual items, adjusting an offer to sell one or more virtual items, matching users for particular circumstances, and/or other adaptations.

The difficulty setting may apply to online games and define how challenging the online games are for the users. Adjusting the difficulty setting may ease how challenging or increase how challenging the online games are by a particular deviancy. The deviancy may be determined based on the determined psychological profile and updates thereof.

Adjusting the means of communication may include adjusting the means of communication made available to be used contemporaneously, made available to be used one at a time, omitted, and/or other adjustments on means of communication. The means of communication may include one or more of a textual chat, instant messages, private messages, voice communications, video communications, in-game communication, out-of-game communication, hybrid communication (i.e., in-game and out-of-game), and/or other means of communication.

Adjusting the offer to sell one or more virtual items may adjust the price (e.g., money, coins, tokens, stars, etc.) the users must pay for the one or more virtual items or other game content. Adjusting the offer to sell one or more virtual items may adjust which virtual items or game content may be offered to the users to purchase. In some implementations, adjusting the offer to sell one or more virtual items includes offering to or omitting to sell bundles or packages of virtual items for purchase in an online store for a game. These adjustments may also include the virtual items included together, the prices of virtual items and other related characteristics.

Matching users may include more accurately matching users for social circumstances, for competition circumstances, and/or other circumstances. Adapting user matching for competition circumstances may be further adapted for various competition styles. Competition styles may include individual racing, group efforts, group racing, friendly competitions, high intensity competitions, and/or other competition styles.

Circumstances may include social circumstances, for competition circumstances, and/or other circumstances. Adapting user matching for competition circumstances may be further adapted for various competition styles. Competition styles may include individual racing, group efforts, group racing, friendly competitions, high intensity competitions, and/or other competition styles.

Figure 3:
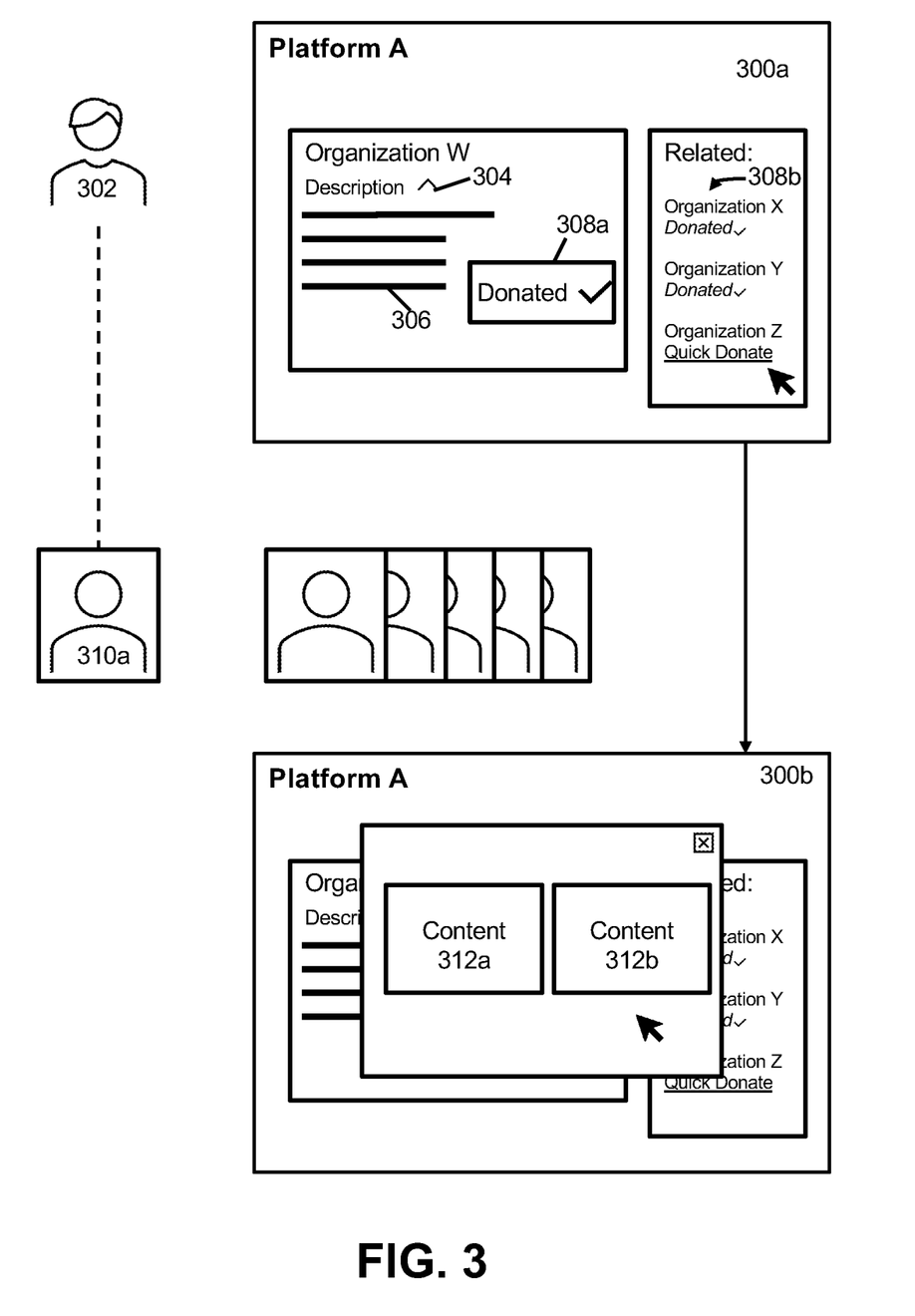
FIG. 3 illustrates an example implementation of the system configured to determine content to present based on interaction information of a given user, in accordance with one or more implementations.

FIG. 3 illustrates an example implementation of the system configured to determine content to present based on interaction information of a given user, in accordance with one or more implementations. FIG. 3 may illustrate a user interface 300a of a Platform A. Platform A may be a charitable/crowdfunding platform where user 302 may donate to one or more people and/or causes. User interface 300a may display an Organization W and Organizations X-Z that are related or not related to Organization W. Organizations X-Z may be of the same category as Organization W and/or of different categories. Organization W and X may be environmental organizations, Organization Y may be an educational organization, and Organization Z may be a political organization. A user 302 may interact with Platform A via user interface 300a and interaction information characterizing the interactions may be obtained by system 100 (of FIG. 1). The interaction information may characterize selection of a user interface element 304 by user 302 to present a description 306 of Organization W, donation 308a to Organization W by user 302, and donations 308b to Organizations X and Y. Based on the interaction information, a psychological profile 310a may be determined to identify user 302 without personal identification information. As user 302 continues to interact with Platform A (e.g., viewing organization descriptions, donations, etc.) and thus the interaction information in ongoingly obtained, psychological profile 310a may be updated (e.g., acting with awareness parameter, impulsiveness parameter, etc.). Based on psychological profile 310a, a user interface 300b (the same as or similar to user interface 300a) may be displayed that includes content 312a and 312b. Content 312a may be a suggestion to subscribe to an online news source that reports on environmental projects and studies. Content 312b may be a promotion to purchase flora at a discount.

Referring back to FIG. 1, in some implementations, the first user and a second user may be interacting with the first online platform. The second user may be different from the first user. Upon determining that the first psychological profile may identify the first user and the second user, the first user and the second user may be considered instances of the first psychological profile. Instances of the psychological profiles may be two or more users that are determined to be identified by the same psychological profile. The instances may be provided at least some of the same content by content providing component 112.

In some implementations, server(s) 102, client computing platform(s) 104, and/or external resources 118 may be operatively linked via one or more electronic communication links. For example, such electronic communication links may be established, at least in part, via a network such as the Internet and/or other networks. It will be appreciated that this is not intended to be limiting, and that the scope of this disclosure includes implementations in which server(s) 102, client computing platform(s) 104, and/or external resources 118 may be operatively linked via some other communication media.

A given client computing platform 104 may include one or more processors configured to execute computer program components. The computer program components may be configured to enable an expert or user associated with the given client computing platform 104 to interface with system 100 and/or external resources 118, and/or provide other functionality attributed herein to client computing platform(s) 104. By way of non-limiting example, the given client computing platform 104 may include one or more of a desktop computer, a laptop computer, a handheld computer, a tablet computing platform, a NetBook, a Smartphone, a gaming console, and/or other computing platforms.

External resources 118 may include sources of information outside of system 100, external entities participating with system 100, and/or other resources. In some implementations, some or all of the functionality attributed herein to external resources 118 may be provided by resources included in system 100.

Server(s) 102 may include electronic storage 120, one or more processors 122, and/or other components. Server(s) 102 may include communication lines, or ports to enable the exchange of information with a network and/or other computing platforms. Illustration of server(s) 102 in FIG. 1 is not intended to be limiting. Server(s) 102 may include a plurality of hardware, software, and/or firmware components operating together to provide the functionality attributed herein to server(s) 102. For example, server(s) 102 may be implemented by a cloud of computing platforms operating together as server(s) 102.

Electronic storage 120 may comprise non-transitory storage media that electronically stores information. The electronic storage media of electronic storage 120 may include one or both of system storage that is provided integrally (i.e., substantially non-removable) with server(s) 102 and/or removable storage that is removably connectable to server(s) 102 via, for example, a port (e.g., a USB port, a firewire port, etc.) or a drive (e.g., a disk drive, etc.). Electronic storage 120 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 120 may include one or more virtual storage resources (e.g., cloud storage, a virtual private network, and/or other virtual storage resources). Electronic storage 120 may store software algorithms, information determined by processor(s) 122, information received from server(s) 102, information received from client computing platform(s) 104, and/or other information that enables server(s) 102 to function as described herein.

Processor(s) 122 may be configured to provide information processing capabilities in server(s) 102. As such, processor(s) 122 may include one or more of a digital processor, an analog processor, a digital circuit designed to process information, an analog circuit designed to process information, a state machine, and/or other mechanisms for electronically processing information. Although processor(s) 122 is shown in FIG. 1 as a single entity, this is for illustrative purposes only. In some implementations, processor(s) 122 may include a plurality of processing units. These processing units may be physically located within the same device, or processor(s) 122 may represent processing functionality of a plurality of devices operating in coordination. Processor(s) 122 may be configured to execute components 108, 110, and/or 112, and/or other components. Processor(s) 122 may be configured to execute components 108, 110, and/or 112, and/or other components by software; hardware; firmware; some combination of software, hardware, and/or firmware; and/or other mechanisms for configuring processing capabilities on processor(s) 122. As used herein, the term "component" may refer to any component or set of components that perform the functionality attributed to the component. This may include one or more physical processors during execution of processor readable instructions, the processor readable instructions, circuitry, hardware, storage media, or any other components.

It should be appreciated that although components 108, 110, and/or 112 are illustrated in FIG. 1 as being implemented within a single processing unit, in implementations in which processor(s) 122 includes multiple processing units, one or more of components 108, 110, and/or 112 may be implemented remotely from the other components. The description of the functionality provided by the different components 108, 110, and/or 112 described below is for illustrative purposes, and is not intended to be limiting, as any of components 108, 110, and/or 112 may provide more or less functionality than is described. For example, one or more of components 108, 110, and/or 112 may be eliminated, and some or all of its functionality may be provided by other ones of components 108, 110, and/or 112. As another example, processor(s) 122 may be configured to execute one or more additional components that may perform some or all of the functionality attributed below to one of components 108, 110, and/or 112.

Figure 2:
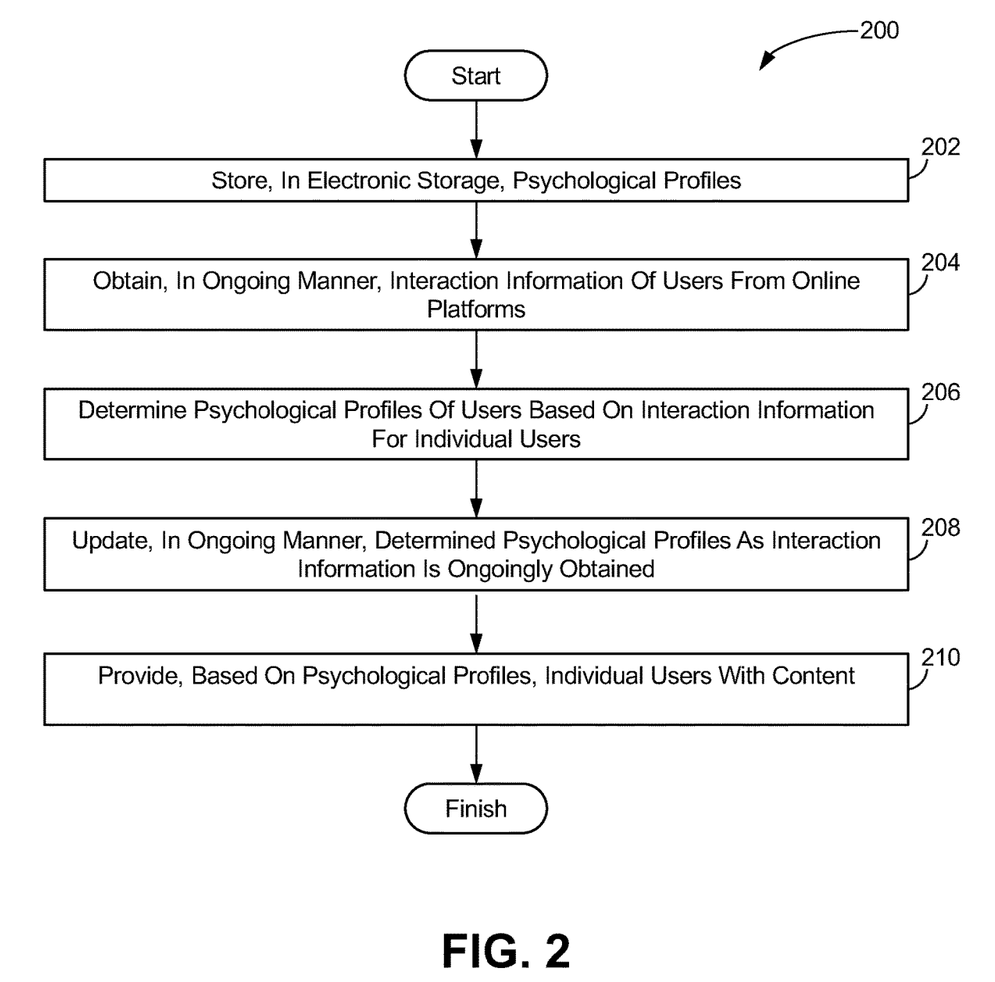
FIG. 2 illustrates a method to determine content to present based on interaction information of a given user, in accordance with one or more implementations.

FIG. 2 illustrates a method 200 to determine content to present based on interaction information of a given user, in accordance with one or more implementations. The operations of method 200 presented below are intended to be illustrative. In some implementations, method 200 may be accomplished with one or more additional operations not described, and/or without one or more of the operations discussed. Additionally, the order in which the operations of method 200 are illustrated in FIG. 2 and described below is not intended to be limiting.

In some implementations, method 200 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 200 in response to instructions stored electronically on an electronic storage medium. The one or more processing devices may include one or more devices configured through hardware, firmware, and/or software to be specifically designed for execution of one or more of the operations of method 200.

An operation 202 may include storing, in electronic storage, psychological profiles. The psychological profiles may characterize a user type and content that suits the user type. Operation 202 may be performed by one or more hardware processors configured by machine-readable instructions including a component that is the same as or similar to interaction information component 108 and/or electronic storage 120, in accordance with one or more implementations.

An operation 204 may include obtaining, in an ongoing manner, interaction information of users from the online platforms. The interaction information may characterize content engaged with by individual users and engagement by the individual users with the content. Operation 204 may be performed by one or more hardware processors configured by machine-readable instructions including a component that is the same as or similar to interaction information component 108, in accordance with one or more implementations.

An operation 206 may include determining psychological profiles of the users based on the interaction information for the individual users. The psychological profiles may identify the individual users without personal identification information. Operation 206 may be performed by one or more hardware processors configured by machine-readable instructions including a component that is the same as or similar to profile tracing component 110, in accordance with one or more implementations.

An operation 208 may include updating, in an ongoing manner, the determined psychological profiles as the interaction information is ongoingly obtained. Operation 208 may be performed by one or more hardware processors configured by machine-readable instructions including a component that is the same as or similar to profile tracing component 110, in accordance with one or more implementations.

An operation 210 may include providing, based on the psychological profiles, the individual users with content. The content provided facilitates further updating of the determined psychological profile and/or may adapt the online platforms to the individual users. Operation 210 may be performed by one or more hardware processors configured by machine-readable instructions including a component that is the same as or similar to content providing component 112, in accordance with one or more implementations.

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

What is claimed is:

1. A system configured to determine content to present based on interaction information of a given user, the system comprising:
   electronic storage configured to store psychological profiles for users; and
   one or more processors configured by machine-readable instructions to:
   obtain, in an ongoing manner, interaction information of users from online platforms, wherein the interaction information characterizes content engaged with by individual users and engagement by the individual users with the content and/or the online platforms;
   determine psychological profiles of the users based on the interaction information for the individual users, wherein the psychological profiles characterize the individual users without personal identification information;
   update, in an ongoing manner, the determined psychological profiles based on the interaction information as the interaction information is ongoingly obtained; and
   transmit, to the online platforms, content for presentation to the individual users based on the psychological profiles that characterize the users by their interaction information and do not identify the personal identification information, wherein the content provided facilitates further updating of the determined psychological profile and/or adapts the online platforms to the individual users.

2. The system of claim 1, wherein the content engaged with by the individual users is related to the online platforms that provide the content, wherein the content includes one or more of a character, a game, a game asset, a recommendation, a promotion, and/or an engagement level of individual ones of the content.

3. The system of claim 1, wherein the engagement by the individual users defines behavior patterns of the individual users with or based on the content, wherein the engagement includes user selection of the content, time spent by the individual users engaging with the content, purchases based on the content, and/or gameplay based on the content.

4. The system of claim 1, wherein the content is provided without assigning a static user identifier to the individual users.

5. The system of claim 4, wherein the psychological profiles determined and ongoingly updated are identifiers for the individual users.

6. The system of claim 1, wherein two or more of the users that interact with different ones of the online platforms are considered instances of the same psychological profile.

7. The system of claim 1, wherein updating the psychological profiles includes determining one or more psychological parameter values and intensity of the one or more psychological parameter values.

8. The system of claim 1, wherein the adaptations to online platforms elicit an intended response, wherein the intended response includes an individual or discrete set of actions by the users.

9. The system of claim 1, wherein the adaptations include one or more of providing a recommendation, providing a suggestion, adjusting a difficulty setting, providing availability to a piece of game content, omitting of game content, providing means of communication, providing a communication, providing an offer to sell one or more virtual items, adjusting an offer to sell one or more virtual items, and/or matching users for particular circumstances.

10. A method to determine content to present based on interaction information of a given user, the method comprising:
    storing, in electronic storage, psychological profiles for users;
    obtaining, in an ongoing manner, interaction information of users from the online platforms, wherein the interaction information characterizes content engaged with by individual users and engagement by the individual users with the content and/or the online platforms;
    determining psychological profiles of the users based on the interaction information for the individual users, wherein the psychological profiles characterize the individual users without personal identification information;
    updating, in an ongoing manner, the determined psychological profiles based on the interaction information as the interaction information is ongoingly obtained; and
    transmitting, to the online platforms, content for presentation to the individual users based on the psychological profiles that characterize the users by their interaction information and do not identify the personal identification information, wherein the content provided facilitates further updating of the determined psychological profile and/or adapts the online platforms to the individual users.

11. The method of claim 10, wherein the content engaged with by the individual users is related to the online platforms that provide the content, wherein the content includes one or more of a character, a game, a game asset, a recommendation, a promotion, and/or an engagement level of individual ones of the content.

12. The method of claim 10, wherein the engagement by the individual users defines behavior patterns of the individual users with or based on the content, wherein the engagement includes user selection of the content, time spent by the individual users engaging with the content, purchases based on the content, and/or gameplay based on the content.

13. The method of claim 10, wherein the content is provided without assigning a static user identifier to the individual users.

14. The method of claim 13, wherein the psychological profiles determined and ongoingly updated are identifiers for the individual users.

15. The method of claim 10, wherein two or more of the users that interact with different ones of the online platforms are considered instances of the same psychological profile.

16. The method of claim 10, wherein updating the psychological profiles includes determining one or more psychological parameter values and intensity of the one or more psychological parameter values.

17. The method of claim 10, wherein the adaptations to online platforms elicit an intended response, wherein the intended response includes an individual or discrete set of actions by the users.

18. The method of claim 10, wherein the adaptations include one or more of providing a recommendation, providing a suggestion, adjusting a difficulty setting, providing availability to a piece of game content, omitting of game content, providing means of communication, providing a communication, providing an offer to sell one or more virtual items, adjusting an offer to sell one or more virtual items, and/or matching users for particular circumstances.

* * * * *